(12) United States Patent
Hennigan et al.

(10) Patent No.: US 9,233,902 B2
(45) Date of Patent: Jan. 12, 2016

(54) PROCESS FOR REMOVING ACETONE FROM A STREAM COMPRISING ACETONE, METHYL ACETATE AND METHYL IODIDE

(75) Inventors: Sean Anthony Hennigan, Hull (GB); David Edward George Jeffers, Woking (GB); Martin John Sellers, Wokingham (GB); Stephen James Smith, Cottingham (GB); Peter John Wilson, Hedon (GB)

(73) Assignee: BP CHEMICALS LIMITED, Middlesex (GB)

( * ) Notice: Subject to any disclaimer, the term of this patent is extended or adjusted under 35 U.S.C. 154(b) by 672 days.

(21) Appl. No.: 13/138,098

(22) PCT Filed: Dec. 23, 2009

(86) PCT No.: PCT/GB2009/002955
§ 371 (c)(1),
(2), (4) Date: Jul. 6, 2011

(87) PCT Pub. No.: WO2010/079317
PCT Pub. Date: Jul. 15, 2010

(65) Prior Publication Data
US 2011/0269988 A1 Nov. 3, 2011

(30) Foreign Application Priority Data
Jan. 6, 2009 (EP) .................................... 09250016

(51) Int. Cl.
*C07C 45/83* (2006.01)

(52) U.S. Cl.
CPC ...................... *C07C 45/83* (2013.01)

(58) Field of Classification Search
CPC ....................................................... C07C 45/83
USPC .......................................... 203/61, 71, 84, 44
See application file for complete search history.

(56) References Cited

U.S. PATENT DOCUMENTS

| 4,252,748 A | 2/1981 | Hoch et al. |
| 4,444,624 A * | 4/1984 | Erpenbach et al. ............. 203/61 |
| 4,717,454 A | 1/1988 | Erpenbach et al. |
| 5,057,192 A | 10/1991 | Zoeller et al. |

FOREIGN PATENT DOCUMENTS

| EP | 0087870 | * | 2/1983 | .............. C07C 51/56 |
| EP | 0 087 870 | | 9/1983 | |
| EP | 0314355 | * | 10/1988 | .............. C07C 69/14 |
| EP | 0 314 355 | | 5/1989 | |
| EP | 0 518 562 | | 6/1992 | |
| JP | 7-324055 A | | 12/1995 | |
| WO | WO 01/46109 | | 6/2001 | |

OTHER PUBLICATIONS

International Search Report for PCT/GB2009/002955, mailed Mar. 1, 2010.
Written Opinion of the International Searching Authority for PCT/GB2009/002955, mailed Mar. 1, 2010.

* cited by examiner

*Primary Examiner* — Paul A Zucker
*Assistant Examiner* — Mark Luderer
(74) *Attorney, Agent, or Firm* — Nixon & Vanderhye P.C.

(57) ABSTRACT

Process for removing acetone from a stream including acetone (A), methyl acetate (MA) and methyl iodide (MI), by (a) introducing the stream into a first distillation zone (FDZ); (b) introducing acetic acid (AA) into the FDZ, by adding AA to the stream or by introducing AA to the FDZ at or above the introduction point of the stream, or a combination thereof; (c) removing from the FDZ an overhead stream including MI and a bottoms stream containing A, MA, AA, and a reduced amount of MI; (d) introducing the bottoms stream into a second distillation zone (SDZ); (e) removing from the SDZ an overhead stream containing MA and MI and a bottoms stream containing A, MA and AA; (f) introducing the bottoms stream from (e) into a third distillation zone (TDZ); removing from the TDZ an overhead stream containing MA and A and a bottoms stream containing MA and AA.

31 Claims, 1 Drawing Sheet

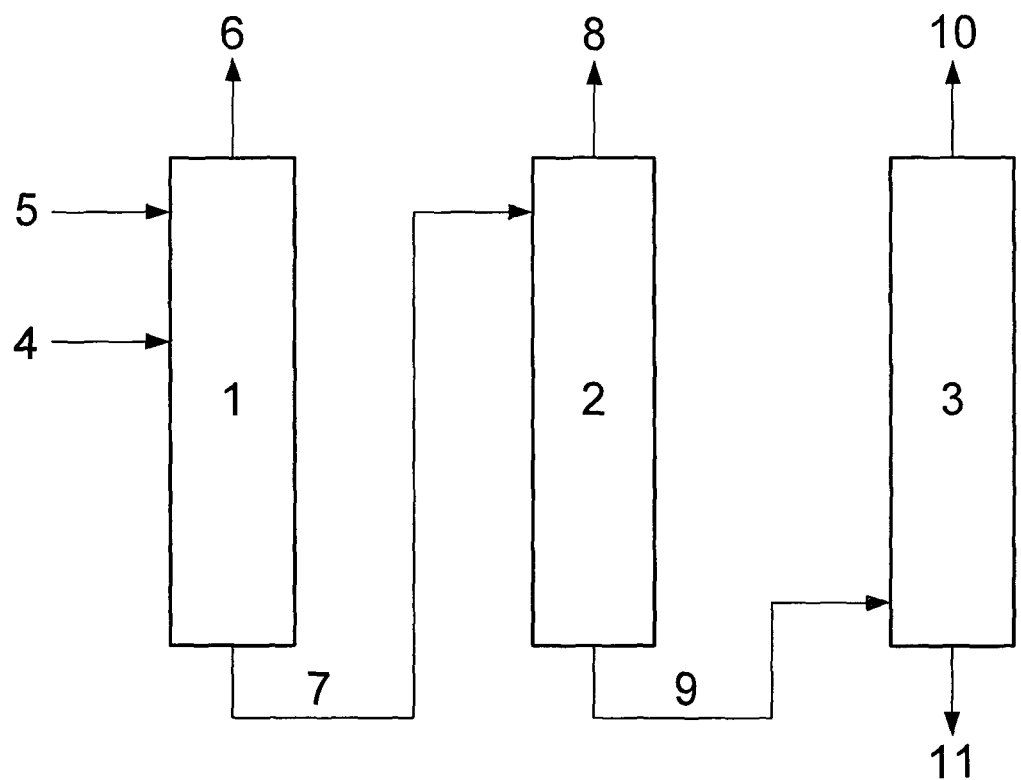

PROCESS FOR REMOVING ACETONE FROM A STREAM COMPRISING ACETONE, METHYL ACETATE AND METHYL IODIDE

This application is the U.S. national phase of International Application No. PCT/GB2009/002955, filed 23 Dec. 2009, which designated the U.S., and claims priority to EP Application No. 09250016.4, filed 6 Jan. 2009, the entire contents of each of which are hereby incorporated by reference.

The present invention relates to a separation process for removing acetone from a mixture comprising acetone, methyl acetate and methyl iodide.

BACKGROUND OF THE INVENTION

Carbonylation processes, such as rhodium catalysed, carbonylation processes, are known, and are industrially important. One such important carbonylation process is for the coproduction of acetic acid and acetic anhydride by the carbonylation of methanol/methyl acetate/water mixtures (for example as described in EP 87870). Such carbonylation processes may be carried out in the presence of methyl iodide.

SUMMARY OF THE INVENTION

Acetone is often produced as a by-product of such carbonylation processes. This by-product can build up in process recycle streams comprising methyl acetate and methyl iodide and may lead to further undesirable by-products and/or reduction of the overall process efficiency. For example, acetone has been reported to inhibit the process catalyst. Further, acetone forms "reducing substances" which cause quality problems in the acetic anhydride product. It has also been discovered that acetone reacts to form tar which must be removed from the process. Acetone is difficult to separate from methyl acetate and methyl iodide because of the formation of azeotropes.

Several processes have, however, been proposed for removing acetone from mixtures of acetone, methyl acetate and methyl iodide.

U.S. Pat. No. 4,252,748 describes a process for removing acetone from the volatile constituents of a reaction mixture which is obtained by carbonylation of methyl acetate in the presence of a Group VIII noble metal and methyl iodide, the process comprising: establishing an acetone to methyl iodide molar ratio of at least 1:10 in the mixture of volatile constituents by introducing acetone, methyl iodide and methyl acetate to the carbonylation reaction; fractionally distilling the mixture of volatile components to separate practically all of the methyl iodide and a portion of the acetone and methyl acetate, the quantity of acetone separated corresponding practically to the quantity supplied to the reaction; distilling off the remaining acetone and methyl acetate from the bottoms of the distillation and recovering the acetone from the methyl acetate/acetone mixture by azeotropic distillation with C5-hydrocarbons followed by extraction of the acetone/C5-hydrocarbon-mixture with water, and fractionation of the acetone from the water phase.

U.S. Pat. No. 4,444,624 describes a process for removing acetone from reaction mixtures originating from the carbonylation of methyl acetate and/or dimethyl ether in which the reaction mixture or its low boiler fraction consisting of methyl acetate, methyl iodide and acetone, is subjected wholly or partially to an extractive distillation with acetic acid in a distilling column comprising 30 trays to distil off pure methyl iodide, and then distilling off an acetone/methyl acetate mixture from the acetic acid extract. The resultant acetone/methyl acetate mixture is said to be separated into its components in art-recognised fashion in a further column with the aid of a C5-hydrocarbon mixture by azeotropic distillation. The distillate is said to be the acetone/C5-hydrocarbon azeotrope and the base product methyl acetate free from hydrocarbons. The acetone/C5-hydrocarbon mixture is said to be separated into its components in known fashion by subjecting it to counter-current extraction with water, the acetone being removed from the water by stripping. Alternatively, acetone/C5-hydrocarbon azeotrope is said to be separated by extractive distillation with acetic acid with the C5-hydrocarbon as distillate and an acetone/acetic acid mixture as base product, which can be separated into its components by fractional distillation.

U.S. Pat. No. 4,717,454 describes a process for removing by-product acetone from reaction mixtures obtained by carbonylation of methyl acetate and/or dimethyl ether in which the by-product acetone is subjected to a condensation at temperatures of 50° C. to 250° C. under pressures of 0.01 to 150 bar so as to obtain predominantly higher-boiling secondary products to be separated in a distillation zone.

U.S. Pat. No. 5,057,192 describes a process for the removal of acetone from a production system in which acetic anhydride is produced by contacting carbon monoxide with a mixture comprising methyl iodide and methyl acetate and/or dimethyl ether in the presence of a catalyst system and acetic acid by the steps comprising: (1) obtaining from the production system a low-boiling stream comprising methyl acetate, methyl iodide, acetic acid and acetone; (2) distilling the stream of step (1) to obtain: (a) an overhead stream comprising methyl acetate, methyl iodide and acetone, and (b) an underflow stream comprising methyl acetate, acetone and essentially all of the acetic acid; (3) extracting the step (2) (a) stream with water to obtain: (a) a methyl iodide phase containing methyl acetate, and (b) an aqueous phase containing methyl acetate, methyl iodide and acetone; and (4) distilling the aqueous phase to obtain: (a) a vapour phase comprising methyl acetate, methyl iodide and minor amounts of acetone and water, and (b) an aqueous stream containing methyl acetate and acetone.

EP0518562 discloses a process for removing acetone from a mixture comprising acetone, methyl acetate and methyl iodide, the process includes the steps: (a) introducing a mixture comprising acetone, methyl acetate and methyl iodide into a distillation zone; (b) introducing water into the distillation zone at one or more points above the point of introduction into the distillation zone of the acetone/methyl acetate/methyl iodide mixture; (c) introducing acetic acid at one or more points at or above the point of introduction into the distillation zone of the acetone/methyl acetate/methyl iodide mixture; (d) removing from the distillation zone a heads product stream comprising methyl acetate and methyl iodide; and (e) removing from the distillation zone water, acetic acid and acetone at one or more points below the introduction point of the acetone/methyl acetate/methyl iodide mixture into the distillation zone.

WO 01/46109 describes a process for the removal of acetone from a mixture which includes a methyl halide promoter, wherein the mixture includes methyl acetate, methyl iodide and acetone, the process includes the steps: (1) introducing a mixture which includes acetone, methyl acetate and methyl iodide into a first distillation zone; (2) withdrawing a side stream having acetone, methyl acetate and methyl iodide from the first distillation zone; (3) introducing the side stream into a second distillation zone; (4) introducing water into the second distillation zone at substantially the same feed point as the side stream feed or at one or more points above the side stream feed; and (5) removing an overhead product comprising methyl acetate and substantially all of the methyl iodide fed to the second distillation zone and at one or more points below the side stream feed point an underflow product comprising acetone, methyl acetate and water.

Whilst the processes as described in U.S. Pat. No. 5,057,192, EP0518562 and WO 01/46109 are generally simpler to operate than the earlier processes described in U.S. Pat. No. 4,252,748, U.S. Pat. No. 4,444,624 and U.S. Pat. No. 4,717,454, the use of water in distillation columns, as is described in U.S. Pat. No. 5,057,192, EP 0518562 and WO 01/46109, in a process to separate acetone from a mixture comprising acetone, methyl acetate and methyl iodide, and which itself has been obtained from a carbonylation process for the production of acetic anhydride or the co-production of acetic acid and acetic anhydride, can however be problematic. In particular, water may end up being recycled back to the process wherein it degrades high value acetic anhydride back to acetic acid.

Further, where the mixture comprising acetone, methyl acetate and methyl iodide has been obtained from a production system in which a mixture comprising methanol, methyl acetate and water is carbonylated to produce acetic anhydride or a mixture of acetic anhydride and acetic acid it is desirable to recover as much methyl iodide as possible. Methyl iodide is both expensive and toxic, thus, loss of methyl iodide may be uneconomical and/or unsafe. In particular, where the mixture comprising methanol, methyl acetate and water is carbonylated in the presence of methyl iodide, for example where the mixture is carbonylated in the presence of free or combined metallic carbonylation catalyst, a catalyst promoter and methyl iodide, it is desirable to recover as much methyl iodide as possible such that it may be recycled back to the production system.

Thus, there remains a need for an improved process for the removal of acetone from a mixture comprising acetone, methyl acetate and methyl iodide as obtained from such a carbonylation process.

According to a first aspect of the present invention there is provided a process for the removal of acetone from a stream comprising acetone, methyl acetate and methyl iodide, said process comprising the steps of:

(a) introducing said stream comprising acetone, methyl acetate and methyl iodide into a first distillation zone;

(b) introducing acetic acid into said first distillation zone, either by addition of acetic acid to said stream comprising acetone, methyl acetate and methyl iodide or by introduction of acetic acid directly to the first distillation zone at one or more points at or above the point of introduction of said stream comprising acetone, methyl acetate and methyl iodide into the first distillation zone in step (a), or a combination of both;

(c) removing from the first distillation zone an overhead stream comprising methyl iodide and a bottoms stream comprising acetone, methyl acetate, acetic acid, and a reduced amount of methyl iodide;

(d) introducing into a second distillation zone the bottoms stream from step (c);

(e) removing from the second distillation zone an overhead stream comprising methyl acetate and methyl iodide and a bottoms stream comprising acetone, methyl acetate and acetic acid;

(f) introducing the bottoms stream from step (e) into a third distillation zone;

(g) removing from the third distillation zone an overhead stream comprising methyl acetate and acetone and a bottoms stream comprising methyl acetate and acetic acid.

The process of the present invention provides an improved process for the removal of acetone from a mixture comprising acetone, methyl acetate and methyl iodide.

Preferably, the process of the present invention is a process for the removal of acetone from a stream comprising acetone, methyl acetate and methyl iodide which stream has been obtained from a production system in which a mixture comprising methanol, methyl acetate and water is carbonylated to produce acetic anhydride or a mixture of acetic anhydride and acetic acid, most preferably a production system which produces a mixture of acetic anhydride and acetic acid. In particular, the process of the present invention avoids extraction of the acetone with water, which water may then be recycled back to the carbonylation process. Further, by maintaining only low levels of water in the respective streams, the streams fed to the first, second and third distillations zones are all single phase streams which simplifies the distillations allowing relatively simple separations. Furthermore, the present invention allows very high recovery of methyl iodide, which methyl iodide may then be recycled back to the production system.

In step (a) the stream comprising acetone, methyl acetate and methyl iodide is introduced into a first distillation zone.

Typically, the stream comprising acetone, methyl acetate and methyl iodide, as initially provided, comprises, by weight, 0 to 40% acetic acid, 10 to 60% methyl acetate, 0.1 to 10% acetone, preferably 0.1 to 3% acetone, 10 to 50% methyl iodide and 0 to 1% water, most preferably less than 0.5% water.

As is clear from the above composition, said stream comprising acetone, methyl acetate and methyl iodide may also contain acetic acid and/or water.

In particular, acetic acid may be present in the stream comprising acetone, methyl acetate and methyl iodide as obtained from the production system in which a mixture comprising methanol, methyl acetate and water is carbonylated to produce acetic anhydride and acetic acid.

For avoidance of any doubt, it is a feature of the present invention that in step (b) additional acetic acid is introduced into the first distillation zone. This may be either by addition of acetic acid to the stream comprising acetone, methyl acetate and methyl iodide prior to its introduction into the first distillation zone, or by introduction of acetic acid directly to the first distillation zone at one or more points at or above the point of introduction of said stream comprising acetone, methyl acetate and methyl iodide into the first distillation zone, or both. The acetic acid flows downwardly in the distillation column and contacts an upward flow of vapour. The acetic acid increases the relative volatility of methyl iodide with respect to methyl acetate and acetone and therefore acts as a selective extractant for methyl acetate and acetone. It will be apparent that for initial streams with acetic acid already therein, less acetic acid may be required to be added in step (b). Typically, acetic acid is added in an amount such that the total amount of acetic acid fed to the first distillation zone is equivalent to 20 to 60% by weight of the total feeds. Typically at least 50%, and more typically 60 to 90% of the total amount of acetic acid fed to the first distillation zone is "additional" acetic acid added in step (b).

The "additional" acetic acid is usually added as a stream comprising at least 95 wt % acetic acid, usually at least 98 wt % acetic acid, and most preferably at least 99 wt % acetic acid. Other components that may be present in minor amounts, if any, include water.

It is preferred that water is substantially absent from the first distillation column. However, it is often difficult to completely preclude water from the stream comprising acetone, methyl acetate and methyl iodide or from the stream comprising the additional acetic acid added to the first distillation column. However, it is important that when water is present that the amount is relatively low. Most preferably the stream comprising acetone, methyl acetate and methyl iodide comprises less than 0.5 wt % water and the stream comprising additional acetic acid comprises less than 1 wt % water.

The first distillation zone acts to remove the majority of the methyl iodide in the stream comprising acetone, methyl acetate and methyl iodide fed to the first distillation zone. Thus, from said first distillation zone are removed an overhead stream comprising methyl iodide and a bottoms stream comprising acetone, methyl acetate, acetic acid, and a reduced amount of methyl iodide. By "a reduced amount of methyl iodide" it is meant that the methyl iodide content of the bottoms stream from the first distillation column is less than the methyl iodide content of the stream comprising acetone, methyl acetate and methyl iodide fed to the first distillation zone. The overhead stream is a substantially pure methyl iodide stream, by which is meant comprising at least 95% by weight, preferably at least 98% by weight of methyl iodide. Where the stream comprising acetone, methyl acetate and methyl iodide has been obtained from a production system in which a mixture comprising methanol, methyl acetate and water is carbonylated to produce acetic anhydride or a mixture of acetic anhydride and acetic acid, all or part of the overhead stream from the first distillation column may be recycled back to the production system.

A typical configuration of the first distillation zone is a distillation column having 20-25 theoretical separation stages. The first distillation zone may be operated at any suitable pressure. A typical operating pressure is 0-3 barg (0-0.3 MPa gauge).

Typically the bottoms stream from the first distillation zone comprises by weight 5 to 15% methyl iodide, 20 to 40% methyl acetate, 20 to 60% acetic acid, 1 to 4% acetone and 0 to 1% water.

In steps (d) and (e) the bottoms stream from the first distillation zone is introduced into a second distillation zone, from which is removed an overhead stream comprising methyl acetate and methyl iodide and a bottoms stream comprising acetone, methyl acetate and acetic acid.

Whilst the first distillation zone acts to remove the majority of the methyl iodide in the stream comprising acetone, methyl acetate and methyl iodide, it can be difficult to remove all of the methyl iodide as a substantially pure methyl iodide overhead stream by a single extractive distillation step without the need for a very large distillation column, or a distillation column having a very high number of theoretical separation stages. Thus, the second distillation zone acts to remove the remainder of any methyl iodide in the bottoms stream from the first distillation zone.

In addition to methyl acetate and methyl iodide the overhead stream from the second distillation zone may comprise minor amounts of acetone and water. The overhead stream typically comprises, by weight, at least 90%, preferably at least 95% methyl iodide and methyl acetate. The stream typically comprises, by weight, less than 4% acetone and less than 1% water. Where the stream comprising acetone, methyl acetate and methyl iodide fed to the first distillation zone has been obtained from a production system in which a mixture comprising methanol, methyl acetate and water is carbonylated to produce acetic anhydride or a mixture of acetic anhydride and acetic acid, all or part of the overhead stream from the second distillation column may be recycled back to the production system.

The bottoms stream from the second distillation zone is essentially free of methyl iodide, by which is meant it comprises less than 10 ppm methyl iodide by weight. The bottoms stream from the second distillation zone typically comprises, by weight, 20 to 40% methyl acetate, 45 to 70% acetic acid, 1 to 4% acetone and 0 to 1% water.

A typical configuration of the second distillation zone is a distillation column having 25-35 theoretical separation stages. The second distillation zone may be operated at any suitable pressure. A typical operating pressure is 0-3 barg (0-0.3 MPa gauge).

In steps (f) and (g) the bottoms stream from step (e) is introduced into a third distillation zone from which is removed an overhead stream comprising methyl acetate and acetone and a bottoms stream comprising methyl acetate and acetic acid.

The third distillation zone acts to remove the acetone as an overhead stream. This stream also comprises some methyl acetate but essentially no methyl iodide, and so may be economically sent for disposal by combustion. Typically, the overhead stream comprises at least 90%, preferably at least 95% by weight of acetone and methyl acetate, typically made up of at least 70% methyl acetate and at least 10% acetone. The overhead stream may also comprise some water, typically up to 10% by weight, but usually comprises essentially no acetic acid (less than 10 ppm by weight).

Typically the bottoms stream from the third distillation zone comprises, by weight, 10 to 40% methyl acetate, 45 to 80% acetic acid, 0.5 to 2% acetone and 0 to 1% water. Where the stream comprising acetone, methyl acetate and methyl iodide fed to the first distillation zone has been obtained from a production system in which a mixture comprising methanol, methyl acetate and water is carbonylated to produce acetic anhydride or a mixture of acetic anhydride and acetic acid, all or part of the bottoms stream from the third distillation zone may be recycled back to the production system.

A typical configuration of the third distillation zone is a distillation column having 30-40 theoretical separation stages. The third distillation zone may be operated at any suitable pressure. A typical operating pressure is 0-3 barg (0-0.3 MPa gauge).

According to a second aspect of the present invention there is provided a process for the production of acetic anhydride or the co-production of acetic anhydride and acetic acid, said process comprising:
  A) carbonylating a mixture comprising methanol, methyl acetate and water in the presence of free or combined metallic carbonylation catalyst, a catalyst promoter and methyl iodide to produce a reaction mixture comprising (1) acetic anhydride or a mixture of acetic acid and acetic anhydride and (2) a stream comprising acetone, methyl acetate and methyl iodide;
  B) recovering the stream comprising acetone, methyl acetate and methyl iodide as a light ends fraction comprising acetone, methyl acetate and methyl iodide from the reaction mixture;
  C) passing said stream comprising acetone, methyl acetate and methyl iodide to a process for the removal of acetone from a stream comprising acetone, methyl acetate and methyl iodide as described herein.

Any of the known metallic carbonylation catalysts may be employed for the carbonylation reaction. Suitable metals include the metals of Group VIII of the Periodic Table of the Elements namely iron, cobalt, nickel, ruthenium, rhodium, palladium, osmium, iridium and platinum. Preferred Group VIII metal catalysts are iridium, osmium, platinum, palladium, rhodium and ruthenium. Particularly preferred is rhodium. It is preferred to employ the metal in the form of a soluble compound such as a salt or a complex of the metal, for example a carbonyl complex. As carbonylation catalyst promoter there is used halogen in free or combined form. The catalyst promoter may comprise quaternary organo-nitrogen compounds, for example N,N-dimethyl imidazolium iodide or N-methyl pyridinium iodide; quaternary organo-phosphorous compounds, for example tetrabutyl phosphonium iodide; and/or alkali metal salts, for example lithium iodide. Suitable carbonylation reaction conditions are described in European patent EP 87870 which is hereby incorporated by reference.

In addition to the catalyst, promoter and methyl iodide the reaction mixture will generally contain acetic acid, acetic anhydride, ethylidene diacetate, and methyl acetate and acetone. The light ends fraction may be separated from the reaction mixture by distillation, preferably fractional distillation.

It will be appreciated by those skilled in the art, that in an integrated carbonylation process wherein a mixture comprising methanol, methyl acetate and water is carbonylated in the presence of free or combined metallic carbonylation catalyst, a catalyst promoter and methyl iodide there are several light ends fraction process recycle streams which comprise acetone, methyl acetate and methyl iodide which may be used in the process of the present invention thereby to prevent the build up of acetone in the carbonylation reaction mixture. Thus in one embodiment, the carbonylation reaction mixture, which is at elevated pressure and temperature, is passed from a reaction zone through a flash zone where its pressure and temperature are reduced. High boiling and involatile catalyst components are recycled to the carbonylation reaction zone from the base of the flash zone. A mixture of light ends fraction together with the carbonylation product(s) is taken overhead from the flash zone. Some or all of the light ends fraction is separated from the carbonylation products by one or more distillation steps for use in the process of the present invention.

BRIEF DESCRIPTION OF THE DRAWINGS

The invention will now be illustrated by way of example only and with reference to FIG. 1 which shows in schematic form a process according to the present invention.

DETAILED DESCRIPTION OF THE INVENTION

In particular, FIG. 1 shows first (1), second (2) and third (3) distillations zones for the removal of acetone from a stream comprising acetone, methyl acetate and methyl iodide. The stream comprising acetone, methyl acetate and methyl iodide is passed to the first distillation zone (1) via line (4). Acetic acid is also passed to the first distillation zone, via line (5), and at a point above the point of introduction of the stream comprising acetone, methyl acetate and methyl iodide.

There is removed from the first distillation zone an overhead stream (6) comprising methyl iodide and a bottoms stream (7) comprising acetone, methyl acetate, acetic acid, with a reduced amount of methyl iodide.

The bottoms stream (7) is introduced into the second distillation zone (2), from which is removed an overhead stream (8) comprising methyl acetate and methyl iodide and a bottoms stream (9) comprising acetone, methyl acetate and acetic acid.

This bottoms stream (9) is introduced into the third distillation zone (3), from which is removed an overhead stream (10) comprising methyl acetate and acetone and a bottoms stream (11) comprising methyl acetate and acetic acid.

EXAMPLE

The Example is based on the process according to FIG. 1. The compositions of the respective streams 4 to 11 are presented in Table 1.

TABLE 1

| | Stream | | | |
| --- | --- | --- | --- | --- |
| | 4 | 5 | 6 | 7 |
| Total flow (mass) | 2764 | 1800 | 684 | 3880 |
| Weight % of: | | | | |
| Acetone | 2.11 | 0 | 0 | 1.48 |
| Methyl Iodide | 36.96 | 0 | 98.3 | 9.00 |
| Methyl acetate | 44.92 | 0 | 0 | 32.00 |
| Water | 0.01 | 0.50 | 0.50 | 0.15 |
| Acetic acid | 16.01 | 99.50 | 1.20 | 57.37 |

| | Stream | | | |
| --- | --- | --- | --- | --- |
| | 8 | 9 | 10 | 11 |
| Total flow (mass) | 600 | 3280 | 112 | 3168 |
| Weight % of: | | | | |
| Acetone | 1.40 | 1.50 | 13.40 | 1.10 |
| Methyl Iodide | 58.20 | 0 | 0 | 0 |
| Methyl acetate | 38.50 | 31.00 | 84.40 | 29.10 |
| Water | 0.40 | 0.11 | 2.20 | 0.03 |
| Acetic acid | 1.50 | 67.40 | 0 | 69.77 |

It can be seen from the above that stream 10 comprises a significant amount of acetone. In fact, just over 25% of the acetone in the stream comprising acetone, methyl acetate and methyl iodide provided to the first distillation zone is removed by the process of the present invention. This is sufficient to prevent "build-up" of the acetone in the recycle streams for a production system in which acetic anhydride and acetic acid are co-produced by the carbonylation of a mixture comprising methanol, methyl acetate and water, reducing the potential production of undesirable by-products and/or reduction of the overall process efficiency that can be caused by acetone build-up.

A further advantage of the process of the present invention is that as well as generally avoiding the use of water (at least deliberately introduced water) in the removal of acetone, over 25% of the water which is present in the first distillation zone (which is predominantly present as an impurity in the acetic acid feed to said zone) is also removed with the acetone in stream 10. Thus, the present invention also reduces the water in the recycle streams for the production system in which acetic anhydride and acetic acid are co-produced.

Furthermore, as can be seen from Table, 1 no methyl iodide is present in streams 9, 10 and 11. Thus, stream 10 may be disposed of economically, without loss of expensive methyl iodide, and the methyl iodide recovered in streams 6 and 8 may be recycled to the production system in which acetic anhydride and acetic acid are co-produced.

The invention claimed is:

1. A process for the removal of acetone from a stream comprising acetone, methyl acetate and methyl iodide, said process comprising the steps of:
   (a) introducing said stream comprising acetone, methyl acetate and methyl iodide into a first distillation zone;
   (b) introducing acetic acid into said first distillation zone, either by addition of acetic acid to said stream comprising acetone, methyl acetate and methyl iodide or by introduction of acetic acid directly to the first distillation zone at one or more points at or above the point of introduction of said stream comprising acetone, methyl acetate and methyl iodide into the first distillation zone in step (a), or a combination of both;
   (c) removing from the first distillation zone an overhead stream comprising methyl iodide and a bottoms stream comprising acetone, methyl acetate, acetic acid, and a reduced amount of methyl iodide;
   (d) introducing into a second distillation zone the bottoms stream from step (c);
   (e) removing from the second distillation zone an overhead stream comprising methyl acetate and methyl iodide and a bottoms stream comprising acetone, methyl acetate and acetic acid;
   (f) introducing the bottoms stream from step (e) into a third distillation zone;
   (g) removing from the third distillation zone an overhead stream comprising methyl acetate and acetone and a bottoms stream comprising methyl acetate and acetic acid.

2. A process according to claim 1 wherein the stream comprising acetone, methyl acetate and methyl iodide has been obtained from a production system in which a mixture comprising methanol, methyl acetate and water is carbonylated to produce acetic anhydride or a mixture of acetic anhydride and acetic acid.

3. A process according to claim 1 wherein the stream comprising acetone, methyl acetate and methyl iodide introduced into step (a) comprises, by weight, 0 to 40% acetic acid, 10 to 60% methyl acetate, 0.1 to 3% acetone, 10 to 50% methyl iodide and 0 to 0.5% water.

4. A process according to claim 1 wherein acetic acid in step (b) is added in an amount such that the total amount of acetic acid fed to the first distillation zone is equivalent to 20 to 60% by weight of the total feeds.

5. A process according to claim 3 wherein acetic acid in step (b) is added in an amount such that the total amount of acetic acid fed to the first distillation zone is equivalent to 20 to 60% by weight of the total feeds.

6. A process according to claim 1 wherein at least 50% of the total amount of acetic acid fed to the first distillation zone is additional acetic acid added in step (b).

7. A process according to claim 3 wherein at least 50% of the total amount of acetic acid fed to the first distillation zone is additional acetic acid added in step (b).

8. A process as claimed in claim 1 wherein the stream comprising acetone, methyl acetate and methyl iodide comprises less than 0.5 wt % water and the stream comprising additional acetic acid comprises less than 1 wt % water.

9. A process according to claim 1 wherein the bottoms stream from the first distillation zone comprises by weight 5 to 15% methyl iodide, 20 to 40% methyl acetate, 20 to 60% acetic acid, 1 to 4% acetone and 0 to 1% water.

10. A process according to claim 3 wherein the bottoms stream from the first distillation zone comprises by weight 5 to 15% methyl iodide, 20 to 40% methyl acetate, 20 to 60% acetic acid, 1 to 4% acetone and 0 to 1% water.

11. A process according to claim 1 wherein the overhead stream from the second distillation zone comprises, by weight, at least 90% methyl iodide and methyl acetate, less than 4% acetone and less than 1% water.

12. A process according to claim 9 wherein the overhead stream from the second distillation zone comprises, by weight, at least 90% methyl iodide and methyl acetate, less than 4% acetone and less than 1% water.

13. A process according to claim 10 wherein the overhead stream from the second distillation zone comprises, by weight, at least 90% methyl iodide and methyl acetate, less than 4% acetone and less than 1% water.

14. A process according to claim 1 wherein the bottoms stream from the second distillation zone comprises, by weight, 20 to 40% methyl acetate, 45 to 70% acetic acid, 1 to 4% acetone and 0 to 1% water.

15. A process according to claim 9 wherein the bottoms stream from the second distillation zone comprises, by weight, 20 to 40% methyl acetate, 45 to 70% acetic acid, 1 to 4% acetone and 0 to 1% water.

16. A process according to claim 11 the bottoms stream from the second distillation zone comprises, by weight, 20 to 40% methyl acetate, 45 to 70% acetic acid, 1 to 4% acetone and 0 to 1% water.

17. A process according claim 1 wherein the overhead stream from the third distillation zone comprises at least 90% by weight of acetone and methyl acetate, up to 10% water by weight, and less than 10 ppm by weight of acetic acid.

18. A process according to claim 14 wherein the overhead stream from the third distillation zone comprises at least 90% by weight of acetone and methyl acetate, up to 10% water by weight, and less than 10 ppm by weight of acetic acid.

19. A process according to claim 1 wherein the bottoms stream from the third distillation zone comprises, by weight, 10 to 40% methyl acetate, 45 to 80% acetic acid, 0.5 to 2% acetone and 0 to 1% water.

20. A process according to claim 14 wherein the bottoms stream from the third distillation zone comprises, by weight, 10 to 40% methyl acetate, 45 to 80% acetic acid, 0.5 to 2% acetone and 0 to 1% water.

21. A process according to claim 17 wherein the bottoms stream from the third distillation zone comprises, by weight, 10 to 40% methyl acetate, 45 to 80% acetic acid, 0.5 to 2% acetone and 0 to 1% water.

22. A process according to claim 18 wherein the bottoms stream from the third distillation zone comprises, by weight, 10 to 40% methyl acetate, 45 to 80% acetic acid, 0.5 to 2% acetone and 0 to 1% water.

23. A process for the production of acetic anhydride or the co-production of acetic anhydride and acetic acid, said process comprising:
   A) carbonylating a mixture comprising methanol, methyl acetate and water in the presence of free or combined metallic carbonylation catalyst, a catalyst promoter and methyl iodide to produce a reaction mixture comprising (1) acetic anhydride or a mixture of acetic acid and acetic anhydride and (2) a stream comprising acetone, methyl acetate and methyl iodide;
   B) recovering the stream comprising acetone, methyl acetate and methyl iodide as a light ends fraction comprising acetone, methyl acetate and methyl iodide from the reaction mixture;
   C) passing said stream comprising acetone, methyl acetate and methyl iodide to a process for the removal of acetone from a stream comprising acetone, methyl acetate and methyl iodide as claimed in claim 1.

24. A process according to claim 23 wherein one or more of (1) the overhead stream comprising methyl acetate and methyl iodide removed from the second distillation zone and (2) the bottoms stream comprising methyl acetate and acetic acid removed from the third distillation zone are recycled to the reaction in which carbonylation of the mixture comprising methanol, methyl acetate and water to produce acetic anhydride or a mixture of acetic acid and acetic anhydride occurs.

25. A process according to claim 6 wherein 60 to 90% of the total amount of acetic acid fed to the first distillation zone is additional acetic acid added in step (b).

26. A process according to claim 7 wherein 60 to 90% of the total amount of acetic acid fed to the first distillation zone is additional acetic acid added in step (b).

27. A process according to claim 11 wherein the overhead stream from the second distillation zone comprises, by weight, at least 95% methyl iodide and methyl acetate, less than 4% acetone and less than 1% water.

28. A process according to claim 12 wherein the overhead stream from the second distillation zone comprises, by weight, at least 95% methyl iodide and methyl acetate, less than 4% acetone and less than 1% water.

29. A process according to claim 13 wherein the overhead stream from the second distillation zone comprises, by weight, at least 95% methyl iodide and methyl acetate, less than 4% acetone and less than 1% water.

30. A process according claim 17 wherein the overhead stream from the third distillation zone comprises at least 95% by weight of acetone and methyl acetate, up to 10% water by weight, and less than 10 ppm by weight of acetic acid.

31. A process according to claim 18 wherein the overhead stream from the third distillation zone comprises at least 95% by weight of acetone and methyl acetate, up to 10% water by weight, and less than 10 ppm by weight of acetic acid.

* * * * *